US009927330B2

(12) United States Patent
Pedrazzini

(10) Patent No.: US 9,927,330 B2
(45) Date of Patent: Mar. 27, 2018

(54) INTERFACING APPARATUS BETWEEN A LABORATORY AUTOMATION SYSTEM AND A PLATFORM FOR HANDLING CONSUMABLES AND LIQUIDS IN THE FIELD OF MOLECULAR BIOLOGY

(71) Applicant: Inpeco Holding Ltd., Qormi (MT)

(72) Inventor: Gianandrea Pedrazzini, Paradiso (CH)

(73) Assignee: INPECO HOLDING LTD., Qormi (MT)

( * ) Notice: Subject to any disclaimer, the term of this patent is extended or adjusted under 35 U.S.C. 154(b) by 97 days.

(21) Appl. No.: 14/405,286

(22) PCT Filed: Jun. 4, 2013

(86) PCT No.: PCT/EP2013/061431
§ 371 (c)(1),
(2) Date: Dec. 3, 2014

(87) PCT Pub. No.: WO2013/182538
PCT Pub. Date: Dec. 12, 2013

(65) Prior Publication Data
US 2015/0147819 A1    May 28, 2015

(30) Foreign Application Priority Data

Jun. 5, 2012   (IT) .............................. MI2012A0975

(51) Int. Cl.
*G01N 1/28*         (2006.01)
*G01N 35/00*       (2006.01)
*G01N 35/10*       (2006.01)
*G01N 35/02*       (2006.01)

(52) U.S. Cl.
CPC ........... *G01N 1/28* (2013.01); *G01N 35/0099* (2013.01); *G01N 35/1065* (2013.01); *G01N 35/028* (2013.01); *G01N 35/10* (2013.01); *G01N 2035/1051* (2013.01); *Y10T 436/2575* (2015.01)

(58) Field of Classification Search
CPC .... G01N 1/28; G01N 35/0099; G01N 35/028; G01N 35/10; G01N 35/1065; G01N 2035/1051; Y10T 436/2575
See application file for complete search history.

(56) References Cited

U.S. PATENT DOCUMENTS

| 6,202,829 B1 * | 3/2001 | van Dyke, Jr. ........ G01N 35/04 198/349.6 |
| 6,358,470 B1 | 3/2002 | Higuchi |
| 2004/0096360 A1 | 5/2004 | Toi et al. |
| 2006/0210435 A1 * | 9/2006 | Alavie ................. G01N 21/253 422/65 |
| 2009/0117620 A1 * | 5/2009 | Fritchie ................ B01L 3/5085 435/91.1 |
| 2010/0126286 A1 * | 5/2010 | Self ........................ G01N 35/04 73/863.81 |

FOREIGN PATENT DOCUMENTS

| EP | 1353183 A2 | 10/2003 |
| WO | 92/05448 A2 | 4/1992 |
| WO | 2008/043463 A1 | 4/2008 |
| WO | 2009/068555 A1 | 6/2009 |

* cited by examiner

*Primary Examiner* — Christopher Adam Hixson
(74) *Attorney, Agent, or Firm* — Jacobson Holman, PLLC.

(57) ABSTRACT

Apparatus for automatically filling wells of plates with biological material from a laboratory automation system for conveying biological samples or reactants contained in test tubes, and automatically routing said plates towards processing modules of said biological material. Said apparatus contains a platform interposed between said laboratory automation system and a handling system of consumable products, which includes a horizontal crosspiece whereon a first robot and a second robot are sliding mounted, the first robot being provided with gripping means of pipettes adapted to collect and release the biological material or the reactant, and a second robot being provided with gripping means of consumable products.

1 Claim, 3 Drawing Sheets

INTERFACING APPARATUS BETWEEN A LABORATORY AUTOMATION SYSTEM AND A PLATFORM FOR HANDLING CONSUMABLES AND LIQUIDS IN THE FIELD OF MOLECULAR BIOLOGY

The present invention relates to an interfacing apparatus between a laboratory automation system and a platform for handling consumables and liquids in the field of molecular biology.

Molecular biology is a branch of biology which studies living beings on basic physiology molecular mechanism level, focusing in particular on interactions between macromolecules, i.e. nucleic proteins and acids (DNA and RNA). Molecular biology often implies a series of techniques for purifying, handling, amplifying (PCR, Polymerase Chain Reaction), detecting, testing and copying (cloning) nucleic acids.

Such operations are performed in highly specialized laboratories using sophisticated apparatuses which operate on biological material samples, appropriately collected beforehand from patients, thus performing the appropriate processing operations listed above in order to achieve a result and issue a medical report.

Typically, a testing cycle of this type may even last for several hours because very often it is necessary to wait for the biochemical reactions to be performed on samples in one of the testers, which sometimes requires very long time to be completed.

The known systems have platforms which accommodate the biological material samples and dispense the contents into specific containers (typically microtiter plates or reaction tubes), named "consumables" in the industry, because they are disposable instruments which must be thrown away after having completed the processing operations on the samples they held.

Separation occurs by means of pipettes which, coupled to appropriate appendixes connected to a robotized arm, collect the biological sample in order to route it into the housings (called wells) of the aforesaid plates. A specific set of pipettes, which is replaced immediately with another for any subsequent liquid collecting operation, typically from several test tubes at the same time, is associated with each liquid collecting operation; it is thus apparent that they are also consumable products, or simply consumables.

Other operation on samples already transferred to the plates may be performed on such platforms, such as for example adding reactants (again by means of pipettes), centrifugation and sealing of the plate; these are preliminary operations to the testing itself in all cases.

Indeed, only at a later time, the plate containing the samples, after having been advantageously identified by means of a barcode reader, is routed to a specific automation system for accommodating and conveying such plates towards other automation or testing devices arranged downstream.

Problems appear in the known solutions because they require the mandatory presence of an operator who manually loads the test tubes, typically accommodated in specific multi-well containers, onto the platform.

Such multi-well containers may be of different size, and thus contain any number of test tubes, but it is apparent that in all cases the presence of an operator is needed to manually load one container after the other, in accordance with the working time of the platform. This is particularly inefficient from the point of view of human resource management in the laboratory, because it forces the operator to be aware at all times and remember to load a new container whenever the processing of a previous container is completed; therefore, the operator cannot continuously focus on other laboratory activities.

An even more noticeable disadvantage is determined by the fact that, with such a manual loading, the test tubes remain blocked on the platform, in the containers, until the processing of all the samples contained in a single multi-well container is completed in the platform itself, i.e. until the operator can replace such a container with a new one.

Such a processing, as mentioned, can last for even several hours, and this thus implies a considerable inefficiency, and a dramatic multiplication of times, considering one container after the other; furthermore, the samples blocked in the platform, besides a few instants in which biological material is collected from them, are mostly standing on the platform without undergoing other operations.

A further disadvantage deriving from the manual loading is the possibility of error, which has severe consequences deriving, for example, from the testing of an "incorrect" sample.

The object of the present invention is to provide a method for automatically loading biological samples on a platform, like those used in the field of molecular biology, thus relieving from this task the laboratory operator in charge, who may then focus on other activities, thus reducing the likelihood of errors in the scope of seeking greater efficiency, i.e. total laboratory automation (TLA) of most operations.

In other words, the target is a walk-away system in which the operator only needs to set up the portion of the system comprising the machines which perform the typical molecular biology activities; once the system has been started, the aforesaid portion of the system must be able to autonomously manage the movements of the various machines which form it, without needing any human intervention.

Another object is to provide a method which prevents the samples from being blocked for hours in the platform, despite the fact that the actual collection of biological material from each one, considered individually, lasts in actual fact only a few seconds. In other words, it is necessary to optimize the collecting process, and thus free the samples from the interaction with the platform nearly instantaneously after collection.

These and other objects are achieved by a method and apparatus for automatically filling wells of plates with biological material from a laboratory automation system for conveying biological samples or reactants contained in test tubes, and automatically routing said plates towards processing modules of said biological material, characterized in that it comprises a platform interposed between said laboratory automation system and a handling system of consumable products, which includes a horizontal crosspiece whereon a first robot and a second robot are sliding mounted, the first robot being provided with gripping means of pipettes adapted to collect and release the biological material or the reactant, and a second robot being provided with gripping means of consumable products, said automation system comprising a control board mutually communicating with a control board of said platform so that the operation of collecting biological material or reactants from the automation system can be simultaneously performed for a variable number of test tubes equal, at most, to the number of said gripping means of said first robot.

These and other features of the present invention will become further apparent from the following detailed description of an embodiment thereof, shown by way of non-limitative example in the accompanying drawings, in which.

A molecular biology platform 1 is located in a test laboratory.

Figure 1:
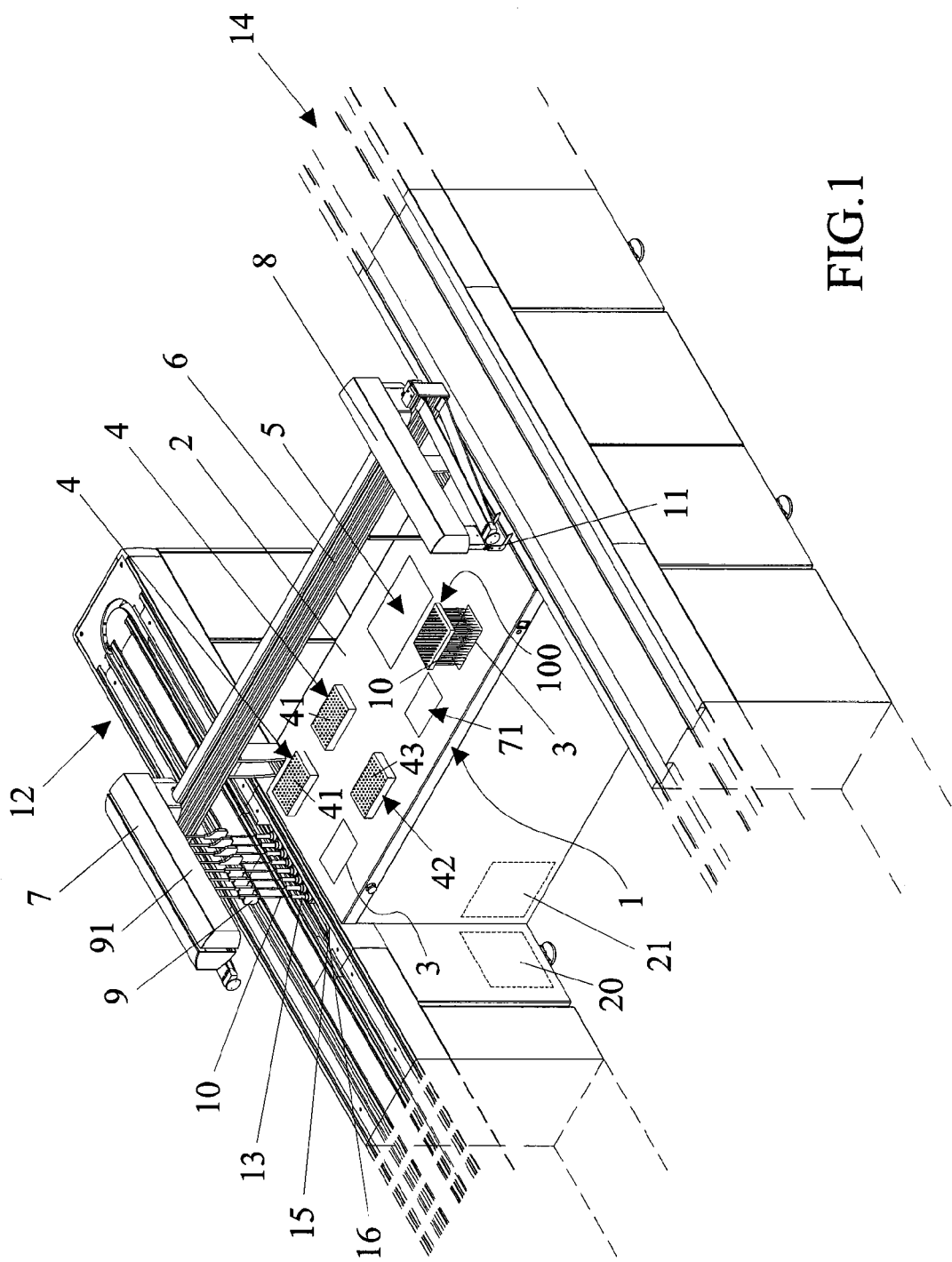
FIG. 1 shows a perspective view of a first embodiment of an apparatus according to the present invention.

Platform 1 comprises a surface 2 with a series of housings 3 for plates 4; such housings 3 are not all mutually equivalent because each housing may correspond to a specific processing operation on the biological material contained in the respective plate 4 accommodated in housing 3 according to the position with respect to surface 2. In FIG. 1, some housings 3 accommodate a plate 4, while the others are empty.

The plates 4 comprise a series of housings or wells 41 adapted to accommodate biological material.

Platform 1 is additionally provided, again along the surface 2, with some devices 5 which may perform operations of various type on plates 4, e.g. sealing or centrifugation of the plate 4 itself.

Platform 1 is surmounted by a horizontal crosspiece 6 on which two robots 7, 8 sliding along said crosspiece 6 are coupled. Gripping devices 9, i.e. fingers, are connected to the first robot 7, each finger being used to couple with pipettes 10, which either collect or release liquids during the various operative steps, as explained in greater detail below. The second robot 8, instead, has a gripping device 11 used to couple, and consequently convey, plates 4 and containers 100 of pipettes 10, i.e. more generically the consumable products, along platform 1 but also at the platform entrance and exit.

A known apparatus similar to platform 1 is described in patent EP-1627687.

Platform 1 interfaces, by means of said crosspiece 6, both with a laboratory automation system 12 for handling biological product containers or test tubes 13 (similar to that described in patent EP-2225567 by the applicant) and with a system 14 used for moving consumable products 4, 100. Plates 4, either empty or containing biological material adapted to be processed and tested by the testing module 18, can move in system 14.

In the following description, we will examine only the interfacing of a platform 1 with a system 12 and a system 14, considering that more than one platform 1 may be used and interfaced with more than one system 12, 14 according to the operative volumes of each test laboratory, in terms of number of biological samples in hand.

The laboratory automation system 12 includes a main lane 15 and a secondary lane 16 along which the biological samples contained in the test tubes 13 are diverted to the height of a first diversion point 24 if they have to interface with platform 1.

In a second embodiment, the automation system 12 comprises a further secondary lane which accommodates the further test tubes, diverted at a second diversion point for purposes which will be explained in greater detail below. An ultrasound sensor, which can discriminate the level of biological sample contained in each of the test tubes along the secondary lane, is present near such a further secondary lane.

Figure 2:
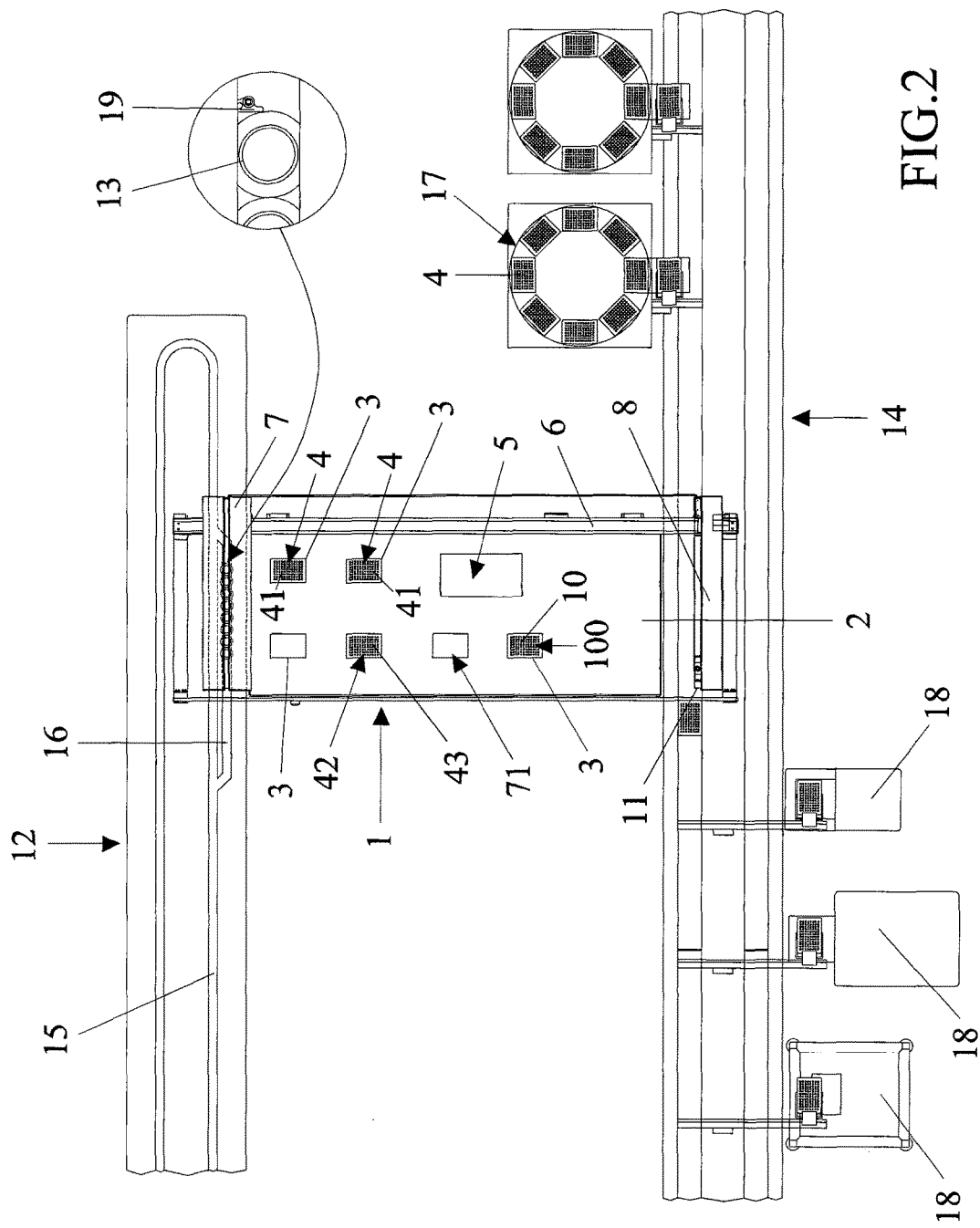
FIG. 2 shows a plan view of the apparatus in FIG. 1.
Figure 3:
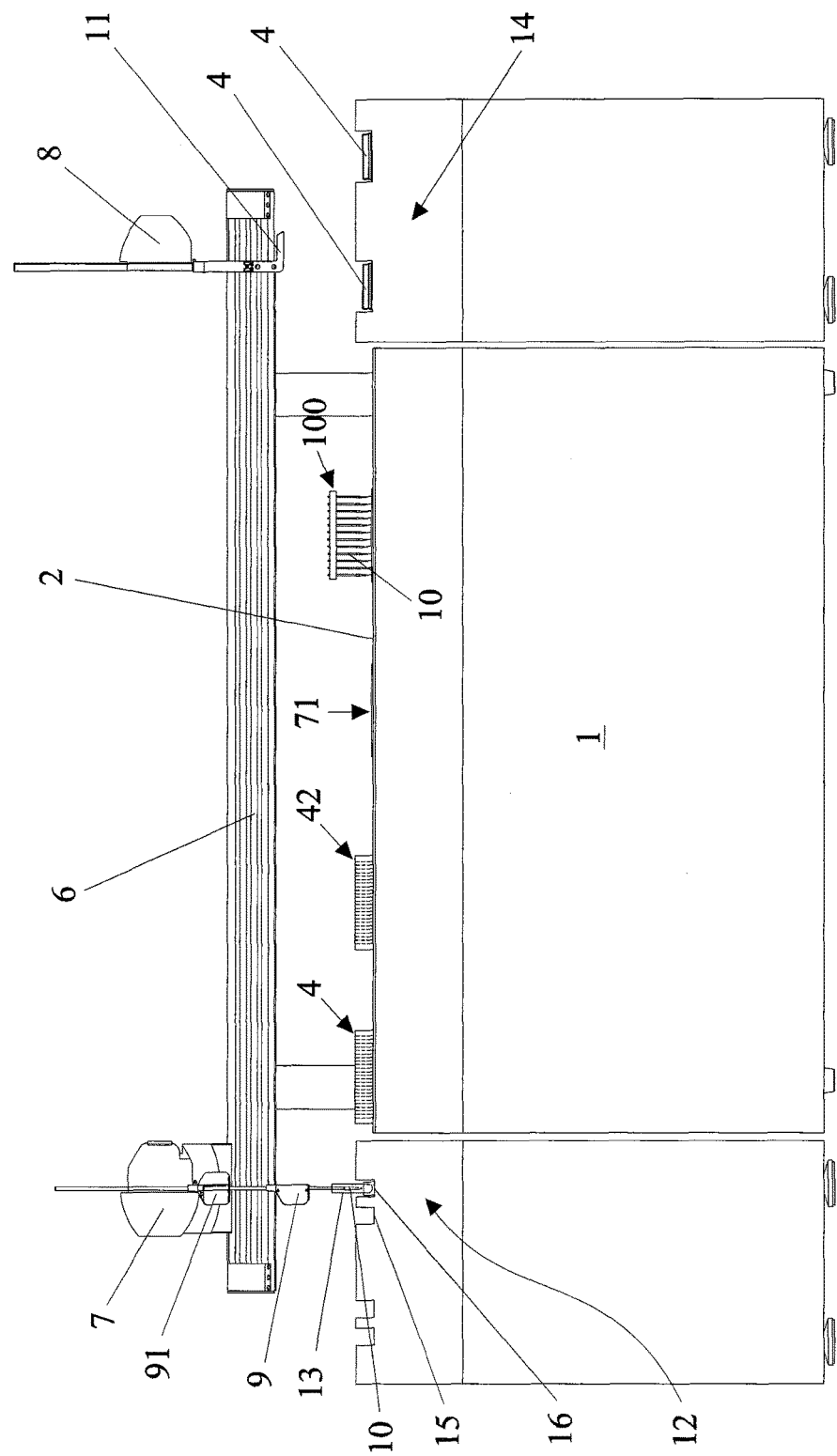
FIG. 3 shows a front view of the apparatus in FIG. 1.

The consumable handling system 14 is located on the other side of platform 1, with respect to the side interfacing with the automation system 12, to which consumable handling system one or storage devices 17 of consumable products (FIG. 2) are connected, i.e. containers (often known as hotels in the prior art), having shelves which can accommodate the containers 100 of pipettes 10 or empty plates 4 to be later filled with biological material. In general, such storage devices 17 thus contain consumable products 4, 100 to be selectively routed (by means of a rotation about the vertical axis of the device itself and a mechanism for moving the various shelves which form it), when needed, to the consumable handling system 14, to then be collected by the second robot 8 and positioned on platform 1.

Operatively, the robot 8 grips an empty plate 4 and a container 100 of new pipettes 10 from system 14, thus positioning them on platform 1 in different housings 3.

The test tubes 13 containing primary samples to be collected are appropriately diverted at the first diversion point 24, from the main lane 15 to the secondary lane 16 of the automation system 12. The first of such test tubes 13 is stopped by a stop gate 19 (FIG. 2) and the following are queued after it. After having diverted the necessary number of test tubes 13, the first robot 7 activates and grips a number of pipettes 10 equal to the test tubes 13 queued along the secondary lane 16 from a housing 3 along platform 1.

The solution can thus be adapted to a variable number of pipettes 10 to be simultaneously gripped while taking into account that there is a maximum number, established by the number of pipettes 10 which may be accommodated on the same row of the container which accommodates them, and that such a number is also the maximum number of test tubes 13 from which biological material can be collected at the same time. The standard size of pipette containers 10, as that of plates 4, is usually of ninety-six wells arranged on rows of eight. Appropriately, the number of gripping fingers 9 connected to the first robot 7 is thus equal to a maximum number (i.e. eight in the embodiment shown in FIG. 1).

The fact that the first robot 7 is activated to favor the gripping of pipettes 10 as soon as the appropriate number of test tubes 13 is achieved along the secondary lane 16 is the result of software interfacing between a control board 20 of the automation system 12 and a control board 21 of platform 1.

Such an interfacing may be performed via a CAN network and a CANopen type communication protocol, and is bidirectional because, as in this case the control board 20 controls the operation of the platform 1 (and in particular of the first robot 7), and in the same way, once the collection has happened, the control board 21 controls the release of the test tubes 13, previously blocked on the stop gate 19 along system 12.

More in general, there is a continuous exchange of information by means of control boards 20 and 21, between system 12 and platform 1; for example, platform 1 may require the collection of biological material from a given number of primary samples, and thus send a request for a given number of test tubes 13 to be diverted to the automation system 12 and the volume of sample which must be collected from each one.

In turn, as mentioned, the automation system 12 informs platform 1 when the appropriate number of test tubes 13 have been diverted along the secondary lane 16 so that platform 1 can start the first robot 7 and collect the primary samples. In detail, the appropriate amount of pipettes 10 is gripped from the specific pipette container 100 located in one of the housings 3 by means of the fingers 9 of the first robot 7, which moves vertically and couples the pipettes 10. Subsequently, the first robot 7 is positioned on the vertical line over the secondary lane 16 which accommodates the test tubes 13 with primary samples. During such a displacement, the fingers 9 open as a fan, by means of appropriate fan opening means 91, so that each single pipette 10 is also on the vertical with respect to each stopped test tube 13.

At this point, the fingers 9 are lowered and the appropriate volume of sample is collected from each test tube 13 (FIG. 1).

The collected samples are then conveyed by the first robot 7 and unloaded into the various wells 41 of a same row of a plate 4 to undergo new operations (e.g. the addition of reactants) managed partially or entirely by platform 1 from this instant in time. The reactants are indeed contained on a different plate 42 in a different housing 3.

It is worth noting that the pipettes 10 are replaced at the end of each biological material or reactant collecting operation; more specifically, the robot 7 firstly positions itself over a basket 71 of platform 1 and unloads the used pipettes 10 by actuating the release of the gripping means of the fingers 9; the robot 7 then positions itself over the container 100 containing new pipettes 10 and operates the gripping of the fingers 9 of said new pipettes 10.

In the meantime, the test tubes 13 from which the biological material was collected are released by retracting the stop gate 19 (as mentioned thanks to the transfer information of collection happened from the control board 21 of platform 1 to the control board 20 of system 12) and thus may return to the main lane 15 to be routed towards other points of the laboratory automation system 12.

Upon arrival of new test tubes 13, from which biological material must be collected, are diverted along the secondary lane 16, and their content is collected by the new pipettes 10, in the meantime gripped by the fingers 9, and unloaded into the wells 41 belonging to the next row of the plate 4.

As already mentioned, one of the housings 3 located at the base of platform 1 is—in the known solutions—dedicated to housing plates 42 with wells 43 containing a different reactant which is added to the biological material samples newly unloaded into the wells 41 of the plate 4; this is conductive to the occurrence of given chemical reactions on the biological sample, in particular to promote the separation of DNA molecules to be analyzed later after the plate 4 is routed to the appropriate instruments 18, located downstream of the plate handling system 14.

Being such wells 43 of reactant already positioned on platform 1 from the beginning, only batch processing is possible in the known solutions because the amount of reactant in the wells 43 is calibrated to be sufficient for a defined number of samples, advantageously a multiple of the maximum number of test tubes 13 from which biological material can be collected at the same time, as described above.

Assuming that there are eight of such samples, batch processing may imply an amount of reactant sufficient, for example, for twenty-four samples, i.e. for three subsequent collecting cycles.

This is particularly inconvenient in the case in which the number of primary test tubes 13 from which collecting biological samples is higher than this number, because after having completed the operation of processing the first twenty-four samples there is no reactant for the latter two, and therefore it is necessary to wait for the new manual filling of the wells 43 of reactant by the operator, which may only occur at the end of the operating cycle of platform 1, which, as mentioned, may last for hours.

The interfacing between the laboratory automation system 12 and the platform 1 allows to overcome this batch processing limit as well, because it is possible to make test tubes 13 also filled with reactant instead of biological material travel along system 12; therefore, reactant can be collected in the same way as described above for primary samples, by diverting an appropriate number of test tubes 13 of reactant along the secondary lane 16. Thereby, it is possible to add an amount of reactant calibrated to the actual number of test tubes 13 from which collecting biological samples without necessarily having to process in batches.

The second embodiment instead relates to the so-called pooling procedures which implies a sharing biological samples from various individuals in a single test tube.

This is conductive to creating blood banks for collecting the most different samples as possible in a few test tubes on which to perform a first, approximate analysis concerning the presence of specific viruses, such as Human Immunodeficiency Virus (HIV), Human Papilloma Virus (HPV) or Herpes Simplex Virus (HSV).

In addition to normal laboratory analysis routine, this procedure is advantageously applied to preliminary testing carried out on samples from individual blood donors (or on other biological materials).

Indeed, it is well known that the presence of the aforesaid viruses is in general rather rarely detected in a normal laboratory analysis routines, and even more so in individuals who express their intention to give blood, and therefore are believed to be healthy; it is therefore preferable to route a test tube containing the biological specimens also of several different individuals mixed together to a specific testing module for discriminating such types of viruses. This saves time and resources by providing a shared sample to be tested by the module test, and thus rapidly allows to reach the certainty that in case of negative result none of the individuals whose sample is in the test tube has the aforesaid virus(es).

In this manner, a preliminary screening for the presence of such given viruses is determined much more rapidly than dedicating a single test tube to each sample. Naturally, in case of positive response, more detailed tests must be immediately ordered to be performed this time on single test tubes, one for each sample of those forming the previous mixed test tube so as to discover which samples, i.e. which individuals, have the detected virus. The automation system 12 can manage the criticality of a situation of this type, by routing the samples to be analyzed in greater depth towards the appropriate modules located in the laboratory along the route of the system 12 itself.

In order to perform such a pooling procedure, a given number of handling devices containing empty test tubes ("children test tubes") are diverted along the further secondary lane, at the second diversion point. In the embodiment, such a number is again equal to eight, in accordance with the number of pipettes 10 of platform 1, for reasons which will be illustrated below. Obviously, also in this case, the first of such empty test tubes diverted along the secondary lane is stopped by a stop gate and the following ones are queued after it.

At the same and in manner similar to that described in the first embodiment above, the handling devices (again eight in this embodiment) containing full test tubes 13 ("parent test tubes"), each of which conveys a biological sample from only one patient, are diverted along the secondary lane 16.

Afterwards, the biological material contained in the parent test tubes 13 is collected as before using the pipettes 10, which this time is unloaded into the respective children test tubes aligned empty and waiting along the secondary lane instead of being unloaded onto the plates 4 on platform 1.

At the end of such an operation, the parent test tubes 13 are released by retracting the stop gate 19. Later on, when eight new handling devices have been further diverted along the secondary lane 16 and are waiting having been stopped at the gate 19, the content is collected again by means of other pipettes 10, and unloaded into the same children test tubes which in the meantime were not released, unlike the previous batch of parent test tubes 13.

The children test tubes are therefore gradually filled with the addition in each of a given amount of biological material from mutually different parent test tubes 13 (and thus individuals) for each cycle. It thus results that each child test tube contains a total sample which is simply the mixture of an equal number of samples from different parent test tubes 13.

The ultrasound sensor is activated at the end of each unloading operation of biological material from the parent test tubes 13 to the children test tubes to detect the filling level of each child test tube each time until a "full test tube" signal is generated after a given number of filling operations, which is followed by the release of the children test tubes by the stop gate; the test tubes therefore return along the main lane 15 of the automation system 12 to then be routed to the appropriate modules used to identify the presence of given viruses, such as—as mentioned—HIV, HPV or HSV, in the mixed samples contained in such children test tubes.

Assuming that a child test tube is filled only after having unloaded the contents of sixteen different parent test tubes 13, it is apparent that the children test tubes each contain samples from sixteen different individuals when they are finally released from the stop gate 1; furthermore, since each incoming sample is associated to a different individual, the total at each release of eight children test tubes is 16×8=128 individuals. It is therefore easy to understand how, once having routed them to the HIV, HPV or HSV testing modules, such children test tubes with mixed samples allow to combine the tests (at least in terms of preliminary screening) for a high number of individuals, thus saving time and resources.

One of the innovative aspects according to the present invention is thus the possibility of collecting biological samples or reactants (to be routed to a molecular biological platform 1 or only in the case of samples to other test tubes waiting along the pooling lane) from test tubes 13 which if needed are diverted along the secondary lane 16 of the automation system 12, and then released after a few instants from the aforesaid collection, being able to return into cycle along system 12 and to be possibly immediately routed to new automation modules or testers which interface with the system 12 itself.

Therefore, the test tubes 13 never leave the automation system 12; this does not occur in the known solutions, in which the test tubes containing biological material are accommodated in large amounts in a specific container which is then manually inserted by an operator on platform 1. Disadvantageously, in this manner the entire number of test tubes must wait on platform 1 for the operative cycle to be completed before being removed again manually by the operator and replaced with another one. This implies that the first test tubes from which biological material is collected must, in all cases, wait for the operations to be performed for the last test tubes allocated in the same container, thus for the subsequent processing operations to be performed for the collected sample and not only the collecting operation, which may last for hours. In the same manner, the latter although arriving later, remain stopped on the platform already for a long time before, i.e. while the first ones are collected. In brief, besides the few instants during which the sample is collected, the test tubes remain idly stopped on platform 1 in the known solutions.

Advantageously, the interfacing of platform 1 with an automation system 12 allows to make test tubes 13 also containing reactants to be combined with the biological material samples so that given chemical reactions occur in the wells 41 of the plates 4 travel along the system. The necessary reactant is made available in this manner gradually in platform 1 only when needed. This allows to overcome the limit represented by the obligation of batch processing of the test tubes deriving from the fact of having a fixed amount of reactant in platform 1 which is sufficient also for a predetermined number of samples.

In general, the automation of the operation process in the solution according to the present invention is higher because the presence of an operator is no longer necessary to manually replace the container of test tubes 13 on which processing has been completed with a new one to be processed on platform 1. Therefore, this is a walk-away system, in which the operator may—in brief—move away from the involved machinery and focus on other tasks in the test laboratory. Advantageously, there is a drastic reduction, or complete elimination, of errors caused by manual, repetitive operations by the operator.

This falls within the scope of the increasingly pressing search for Total Laboratory Automation (TLA), and thus a greater efficiency in a test laboratory in which molecular biology-related activities are performed, thus substantially cancelling out the possibility of human error.

The invention thus devised is susceptible to many changes and variants, all falling within the scope of the inventive concept.

In practice, the materials used as well as the shapes and size may be any, according to needs.

The invention claimed is:

1. A method for automatically transferring biological material and reactants from a laboratory automation system for conveying a plurality of single test tubes containing biological material and a plurality of single test tubes containing reactants, to a handlings system for moving plates with wells with biological material to be tested,
   wherein the laboratory automation system comprises a main lane and a secondary lane for conveying the plurality of said single test tubes and a stop gate at said secondary lane for blocking the plurality of said single test tubes,
   wherein the handling system comprises means for moving the plates with wells to testing modules, and
   wherein the method comprises the following steps:
   in said laboratory automation system, conveying a plurality of said single test tubes containing biological material to be tested and a plurality of said single test tubes containing reactants for biological material to be tested towards a platform interposed between the laboratory automation system and the handling system, said platform housing plates and containers containing a plurality of new pipettes and comprising a horizontal crosspiece whereon a first robot and a second robot are slidingly mounted,
   diverting a plurality of said single test tubes containing biological material to be tested from said main lane to said secondary lane of said laboratory automation system,
   diverting a plurality of single test tubes containing reactants for said biological material to be tested from the main lane to the secondary lane of said laboratory automation systems, linearly queuing a plurality of said single test tubes containing biological material to be tested and a plurality of said single test tubes containing reactants for said biological material to be tested, at said stop gate of said secondary lane, by said first robot, gripping a linear sequence of new pipettes from a container by a linear sequence of fingers for gripping pipettes, moving said linear sequence of pipettes over said test tubes linearly queued at said stop gate of the laboratory automation system, collecting biological material or reactant from said test tubes after lowering said fingers into said test tubes, conveying the collected biological material or reactant over wells of a plate housed in a housing of said platform, releasing the collected biological material or reactant into said wells of a plate, and releasing the used pipettes into a basket of the platform, by said second robot, gripping plates with wells filled with biological material to be tested and moving them to said handling system, gripping plates with empty wells from the handling system and move them to housings of the platform, gripping containers of containing a plurality of new pipettes from the handling system and moving them to housing of the platform, said platform being also provided with a control board mutually communicating with a control board of the laboratory automation system, so that the number of the pipettes to be gripped by the fingers of the first robot is equal to the number of test tubes linearly queued at said stop gate of the laboratory automation system, the maximum number of pipettes being equal to the number of pipettes accommodated on the same row of the container.

\* \* \* \* \*